(12) United States Patent
Kutsch et al.

(10) Patent No.: US 7,156,637 B1
(45) Date of Patent: Jan. 2, 2007

(54) APPARATUS FOR PRODUCING DENTAL PROSTHESES

(76) Inventors: V. Kim Kutsch, 1155 Twin Hills Dr., Jefferson, OR (US) 97352; Robert J. Bowers, 3170 26th Ave., SE., Albany, OR (US) 97322

( * ) Notice: Subject to any disclaimer, the term of this patent is extended or adjusted under 35 U.S.C. 154(b) by 0 days.

(21) Appl. No.: 11/286,416

(22) Filed: Oct. 24, 2005

Related U.S. Application Data

(62) Division of application No. 10/166,429, filed on Jun. 10, 2002, now abandoned.

(60) Provisional application No. 60/299,286, filed on Jun. 19, 2001.

(51) Int. Cl.
*B29C 45/74* (2006.01)

(52) U.S. Cl. .................... 425/178; 264/17; 264/18; 425/542; 425/547; 425/550

(58) Field of Classification Search ........... 425/178, 425/542, 547, 550, DIG. 11; 264/17, 18
See application file for complete search history.

(56) References Cited

U.S. PATENT DOCUMENTS

| | | | |
|---|---|---|---|
| 5,302,104 A | 4/1994 | Ueda | 425/178 |
| 5,635,545 A | 6/1997 | Oxman et al. | 523/115 |
| 5,869,548 A | 2/1999 | Ikushima et al. | 523/116 |
| 5,975,906 A | 11/1999 | Knutson | 433/226 |
| 6,231,337 B1 | 5/2001 | Boyd | 433/6 |
| 6,267,596 B1 | 7/2001 | Kalfax | 433/178 |
| 6,287,490 B1 | 9/2001 | Rheinberger et al. | 264/17 |
| 6,335,385 B1 * | 1/2002 | Gorlich et al. | 425/178 |

* cited by examiner

*Primary Examiner*—Tim Heitbrink
(74) *Attorney, Agent, or Firm*—Lori M. Friedman

(57) ABSTRACT

Disclosed are an apparatus, materials, devices and methods for the use of a variety of thermoplastic resins in fabricating dental prostheses without the use of expensive hot-press equipment unavailable to most dental laboratories. The prostheses made by the process and materials disclosed herein provide more attractive and longer lasting prostheses with significant savings in both costs and materials. Among the aims of the technology disclosed is to save time and money for the dental industry (dentists, dental labs) and the dental consumer/patient.

17 Claims, 6 Drawing Sheets

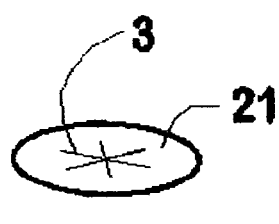  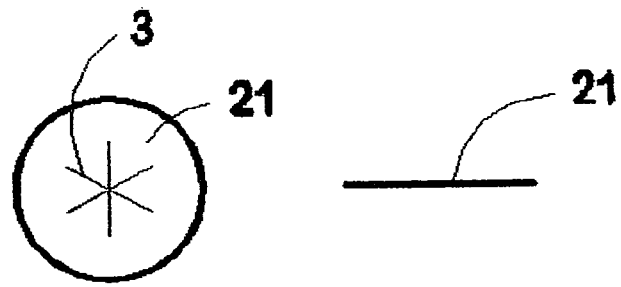
FIG. 5(a)   FIG. 5(b)   FIG. 5(c)
 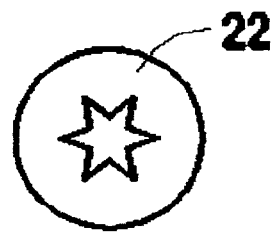 
FIG. 5(d)   FIG. 5(e)   FIG. 5(f)
FIG. 5

APPARATUS FOR PRODUCING DENTAL PROSTHESES

RELATED PATENT APPLICATIONS

This is a utility patent application that is a divisional of prior patent application Ser. No. 10/166,429 filed Jun. 10, 2002 now abandoned that claims the benefit of provisional application No. 60/299,286 filed Jun. 19, 2001.

FIELD OF THE INVENTION

The present invention is directed to new methods and materials that allow a dental laboratory to produce strong and durable temporary, provisional or permanent prostheses and base plates for dentures. More specifically, the invention is directed to using thermoplastic resins, traditionally used in hot press dental lab equipment to make prostheses in an injection molding/extrusion process, using cold press dental laboratory equipment.

BACKGROUND OF THE INVENTION

For many years dentistry has enhanced the quality of life of mankind by providing crowns for damaged, decayed or disfigured teeth. When a tooth is partially broken off, is disfigured or has been damaged by decay, a modern dentist can restore the tooth both in function and appearance to a desired external shape by applying a crown. As commonly practiced today, a dentist first takes an impression employing a plastic material of the patient's tooth or teeth. In some cases, an impression will include all of the patient's upper teeth or all of the patient's lower teeth.

From such impression, a model is easily made by filling the impression with plaster or stone that hardens and, after hardening, is easily removable from the soft plastic impression to faithfully replicate a patient's upper or lower teeth, including the adjacent gingival areas. The dentist then prepares the damaged tooth to receive a crown by removing external portions. To do this, the dentist grinds away external parts of the tooth to reduce the total dimensional size of the tooth to be crowned so that all exterior portions thereof are confined within an area less than that of the desired crown. After the tooth has been prepared by removing exterior portions, a second impression is taken from which a second plaster model is made.

These plaster models are then sent to a dental laboratory where a laboratory technician manufactures a crown. After the crown is completed, it is returned to the dentist who then cements or otherwise bonds it in place on the patient's prepared tooth.

This procedure works satisfactorily except that it takes from several days up to several weeks from the time the dentist makes the impressions until the crown is returned to the dentist from the lab for insertion in the patient's mouth. Typically when a tooth is prepared to receive a crown it is very visually distractive, sensitive and vulnerable. To enable a patient to function both physically, that is to masticate food, and to function socially, that is to have a reasonable appearance, the typical procedure is that the dentist forms a temporary crown by molding temporary crown forming material on the prepared tooth and shaping it and hardening it in the patient's mouth so that the temporary crown will last until the permanent crown made by the dental laboratory is returned to the dentist ready for insertion in the patient's mouth.

The crown procedure is for restoration of a single tooth. Restoration of multiple teeth or multiple missing teeth requires dental prostheses. Dental prostheses are divided into two categories, fixed and removable. Fixed prostheses are tooth and/or implant supported bridges that are bonded or cemented into place and are not routinely removed by the patient. Removable prostheses include: partial dentures, complete or full dentures, bite or occlusal appliances, orthodontic appliances, snoring and sleep apnea appliances. Partial dentures are tooth, tissue and/or implant supported and are removable by the patient for routine cleaning and home care. Complete dentures are tissue or implant supported, as the patient has no remaining teeth on the maxilla, mandible, or both. The occlusal, orthodontic, snoring, mouth guard and sleep apnea appliances may be supported by tooth, implant, tissue or a combination thereof.

Temporary and provisional prostheses are not made by the dentist but are generally fabricated by a dental laboratory. The materials available to the lab for their construction often do not hold up well to extended use in the mouth. Restoration for a patient receiving implants may require a provisional restoration to last a year or more, and maintain the vertical dimension of the patient's bite during that time. Partial dentures are problematic in that they require a metal substructure for support. Complete dentures are typically made with a cold curing acrylic resin, which is porous, has residual free monomer, and absorbs odors, stains and bacteria.

Preparing a temporary prosthesis has been a problem in the dental profession for many years. Such temporary prostheses frequently break or dislodge before the patient returns to the dental office to receive the permanent prosthesis. Problems associated with prostheses for the dentist and dental laboratory include the equipment used for making prostheses, which vary greatly between laboratories. The materials used for making them vary as well depending on which equipment a particular dental laboratory uses.

The equipment can be categorized as hot press or cold press. Of the approximately 40,000 dental laboratories currently operating in the U.S., only about 1.5% have access to hot press equipment. It is the hot press equipment, made by companies including Dental D, Pressing, Flexite, Dentsply FRP and Valplast that currently use thermoplastic resins to make temporary, provisional and permanent prostheses. Thermoplastic resins can be used, for example, to make a temporary or provisional fixed bridge, the substructure framework for a partial denture, or the baseplate of a partial or complete denture. Prostheses made from thermoplastic resins look more natural in the patient's mouth and are stronger and less subject to problems such as allergic reactions or damage from porosity.

Not only is the number of dental laboratories with thermoplastic resin capability small, each equipment manufacturer requires special tools for their use. For example, certain existing thermoplastic dental resin systems require the use of a special oven with a disposable aluminum/tin tube or cylinder and/or Teflon plunger to press a thermoplastic dental prosthesis. These ovens are expensive, costing several thousand dollars and the tubes they require to contain the resin are expensive (costing about $2.00 apiece) and can only be used once. The metal tubes may contaminate the thermoplastic resins held inside of the tubes while they are being melted by imparting a gray discoloration to the prostheses. These tubes are also uniquely sized by each manufacturer; so that one manufacturer's thermoplastic material and tubes cannot be used in another manufacturer's oven and injection molding system.

The difficulties and expense in using hot press injection molding equipment for temporary prostheses are solved by the instant invention. The materials and processes described herein allow the use of more aesthetic, stronger, safer and functional thermoplastic resins in temporary prostheses without the use of expensive hot press machines and materials, including special one-use aluminum tubes.

In the past, various patents have issued that deal with materials and methods for making dental prosthesis. For example, in U.S. Pat. No. 5,869,548, Ikushima describes a dental material that is a core ceramic material that is infused with resin to create a block of tooth colored material which is used in a CAD/CAM device to create a dental prosthesis.

In U.S. Pat. No. 5,302,104 Ueda describes a resin denture base molding apparatus which uses acrylic resin for a denture baseplate. The patent is concerned with vertical guide rods and adjustable tables, their container means requires pressure to "break" it. In U.S. Pat. No. 5,635,545, Osman uses various thermoplastic resins which are imprinted with a heat-stable custom shape custom shape memory after it is processed, primarily for making impressions in the mouth.

In U.S. Pat. No. 6,287,490 Rheinberger discloses a method for manufacturing dental prostheses. This patent uses light and pressure to create a polymerizable resin on a model.

In U.S. Pat. No. 6,231,337 Boyd discloses a method of making a dental mouthpiece. This patent uses a light polymerizable resin material to create a mouthguard in the mouth.

In U.S. Pat. No. 5,975,906 Knutson describes a dead-soft polymer dental strip to create a dental prosthesis in the mouth.

In U.S. Pat. No. 6,267,596 Kalfax discloses a dental appliance that uses a resin as a swing lock mechanism to hold a dental appliance in contact with teeth.

The prior art patents that deal with fashioning dental appliances in the patient's mouth do not result in a properly fitted dental prosthesis as does the instant invention. In U.S. Pat. No. 5,302,104 Ueda uses acrylic resin for a denture baseplate that breaks under pressure. The instant invention uses a pre-perforated container that will separate under light pressure. The instant containment means can also be an open ended bag that does not require pressure to rupture or "break" it.

There has not been a patent found or device known that can accomplish the creation of dental prostheses in the low cost, efficient manner accomplished and explained herein by applicants.

SUMMARY OF THE INVENTION

It is an object of the instant invention to replace various features common in hot press dental laboratory equipment, such as uniquely sized metal tubes of the currently available hot press dental laboratory equipment, with a variety of containment and delivery means for thermoplastic materials to be heated separately in an oven or thermal jacket and then made into dental prostheses in a cold press injection molding machine of the present invention. The delivery and containment means used herein may be in the form of a flexible metal foil bag, foil burst pouch, syringe, ingot, a resin cylinder, fiberglass, metal, polyester film, fabric, disc, resin cylinder, or woven material.

The thermoplastic resins that may be used in the equipment of this invention are selected from the group consisting of homopolymers and copolymers acetal, acrylic, polycarbonate, polystyrene, polyester, polyamide, polyethylene, polypropylene, polysulfone, polyphthalamide resins and nylon, as well as compatible mixtures of these materials.

The cold press molding apparatus of this invention, the various user-friendly container means that hold said resins, the various combinations and groups of these materials, and methods for fabricating sturdy and attractive dental prostheses from them will be described in detail shortly.

DEFINITIONS USED IN THIS INVENTION

The following definitions are provided solely for the benefit of the reader, and should not be construed to limit the terms to any specific examples provided. They should also not be construed to be narrower than those accepted by persons of ordinary skill in the art.

In this invention, a 'temporary' prosthesis is one that is meant to be in the patient's mouth for a time period that may be as long as several weeks. Likewise, in this invention a 'provisional' prosthesis is meant to be in the patients mouth for a period of months, up to about a year or longer.

In this invention, a 'burst pouch' will refer to a packet of thermoplastic resin that remains intact until it is heated and then place in the cold press machine.

In this invention, the term 'stone' will describe a gypsum product that, when combined with water in proper proportions, hardens in a plaster-like form. This term is in common usage in operative dentistry.

In this invention, the word 'invest' will mean to surround, envelop or embed in an investment material, such as gypsum or stone, to form a cast or mold. Similarly 'investment' will mean a process used to cast a mold.

In this invention, the terms 'injection mold' and 'injection molding' will refer to the process by which pre-measured amounts of molten material is dispensed into a mold and formed thereafter into dental prostheses In this invention, both the mold and the prosthesis made from the mold will be referred to by reference numeral 8. The term 'mold' as used in dentistry and this invention specifies the shape of the prosthesis made from it.

BRIEF DESCRIPTION OF THE DRAWINGS

FIG. 5 depicts the disc of the present invention in both its ruptured and unruptured states.

DETAILED DESCRIPTION OF PREFERRED EMBODIMENTS

Figure 1:
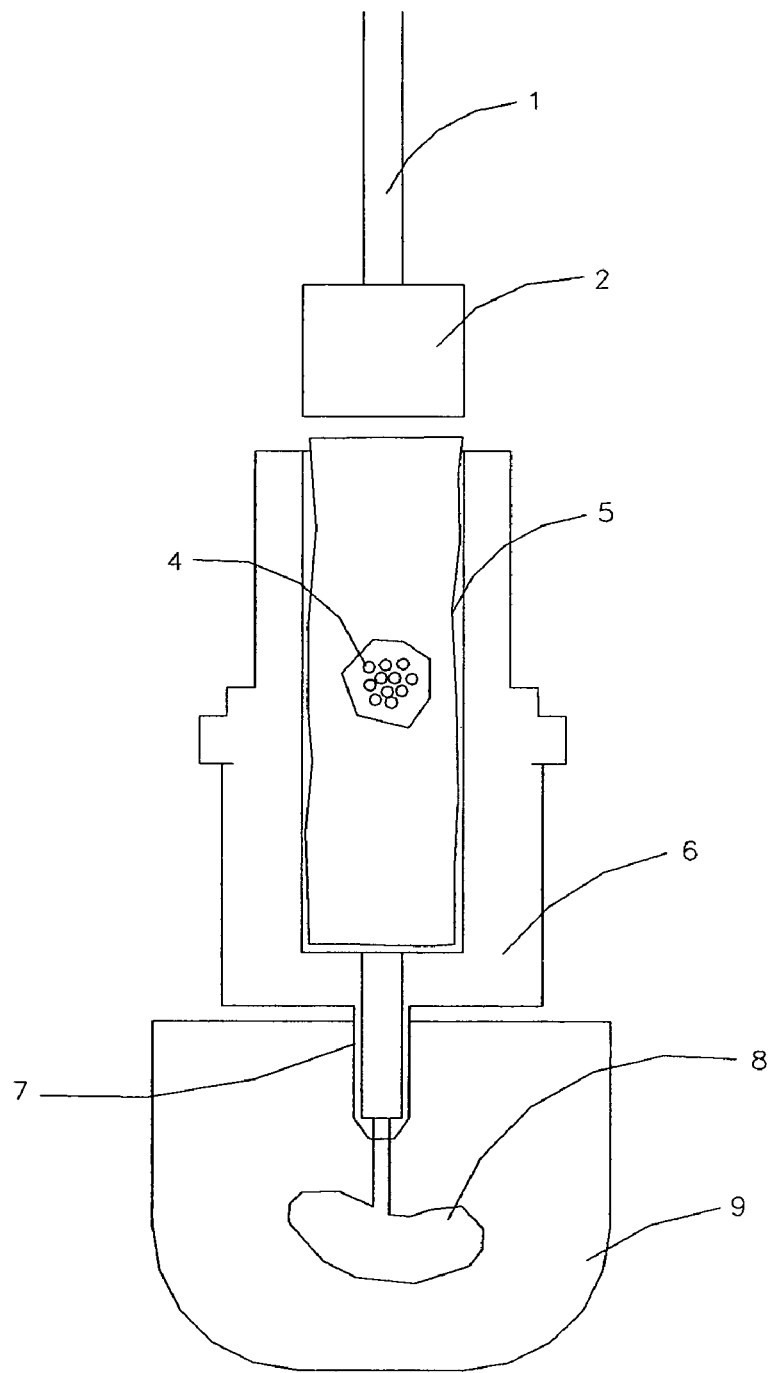
FIG. 1. is a schematic of the cold press machine of the invention depicting its features, wherein a thermoplastic resin is independently heated and is then injection molded into a dental prosthesis.

As shown in FIG. 1, the standard injection molding tube prior art cold press injection molding machine used in dental laboratories is replaced with an injection tube 6 that is made of metal, such as stainless steel, brass, or aluminum, copper or an alloy thereof that has sufficient mass to act as a heat sink. The thermoplastic resin material 4 is dispensed into this tube via containment/delivery means 5, and is then placed into heating means. For purposes of this invention, heating means may be a standard dental laboratory oven, an accessory heating oven, or a thermocouple jacket/heating element 12 (shown in FIG. 4) placed around the injection tube and heated to the melting temperature of the thermoplastic resin 4.

When the resin 4 has reached sufficient temperature to become fluid, the tube is placed into the cold press injection molding machine of this invention. The heating means may be removed or left on the injection tube 6 during the injection procedure. The piston 1 is attached to the plunger 2 which presses the fluid resin 4 through the nozzle 7 and into the mold of the prosthesis 8 contained within the flask 9. The injection tube 6 has sufficient mass to maintain the melting temperature of the thermoplastic resin 4 while it is being injected into the mold of the prosthesis 8. The finished prosthesis 8, replicates the mold used to create it.

Figure 2:
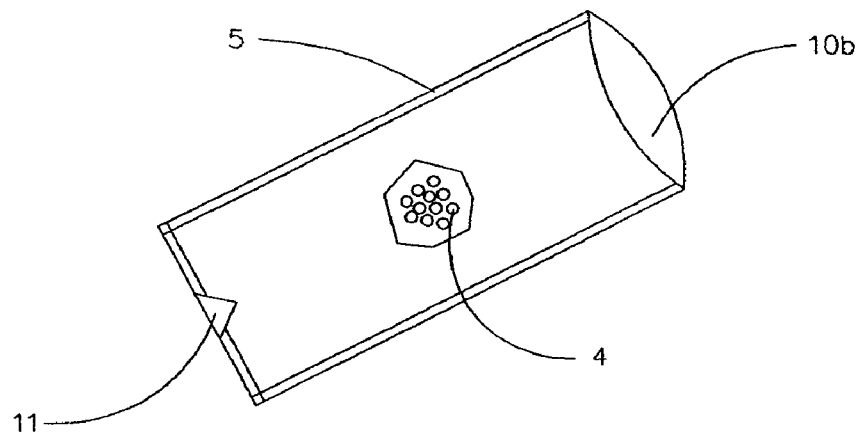
FIG. 2 depicts the containment means for thermoplastic resin as either a sealed, prepackaged burst pouch or an open container of a foil or woven bag
Figure 2:
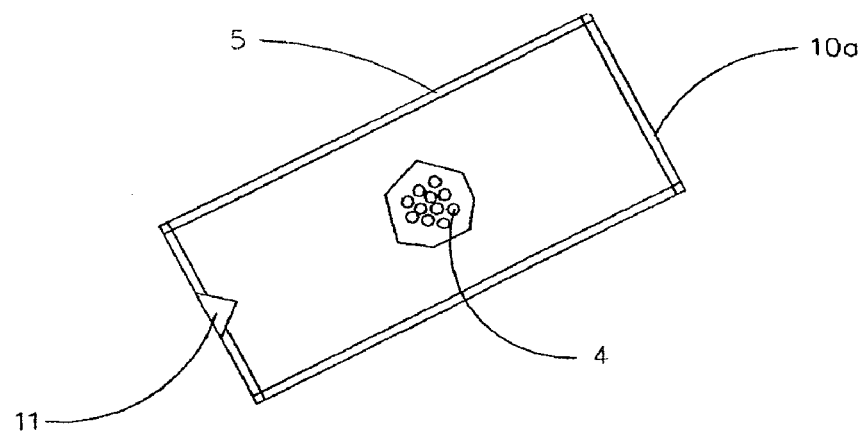
Figure 3:
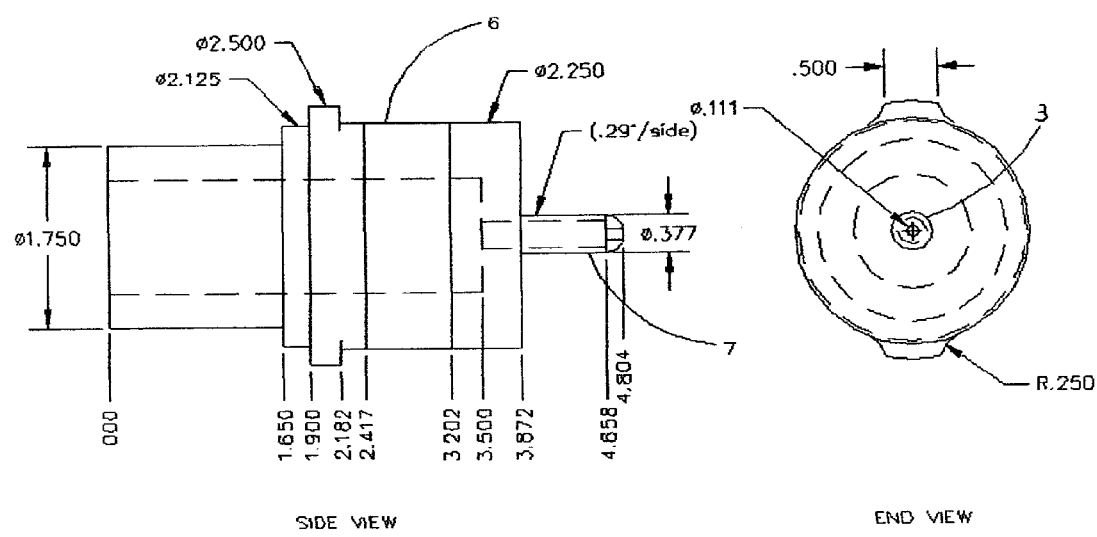
FIG. 3*a* is a detailed mechanical drawing of a side view of the injection tube of this invention, including dimensions.
FIG. 3*b* is a detailed mechanical drawing of an end view of the injection tube of this invention, including dimensions.

In a preferred embodiment of this invention, pre-dispensed or prepackaged amounts of thermoplastic resinous material 4 as shown in FIG. 2 allow for separate oven heating and then employing a cold press injection molding (FIG. 1) machine to press the resinous material 4 into a warmed flask 9 to mold a dental prosthesis 8. In this invention, a flask is 9 a metal form used to contain the two halves of the stone mold (not shown) for the dental prosthesis 8 formed by the injection molding process of this invention.

The containment/delivery means 5 may also be a solid rod of the resin 4 that is a monochromatic color or it may contain a gradient of color. Materials that comprise the containment/delivery means 5 may be a packet of thermoplastic resin 4 that remains intact until it is heated and then place in the cold press machine 20 of this invention. The containment/delivery means 5 may be made of metal or polymer that has a fusion temperature higher than that of the thermoplastic resin 4 that it contains. It also may be made of foil, woven material, or the like. If the containment/delivery means 5 pictured in FIG. 2 is a burst pouch, it will have an open end 10*b*, a sealed end 10*a*, and a notch 11 that control the bursting of the pouch and contains the material in the injection tube 6.

In a preferred embodiment of this invention, the containment/delivery means is a burst pouch 5 made of the same thermoplastic resin 4 that it contains. In this case, there is no material left over when the prosthesis 8 is made. If the material of the burst pouch 5 is not the same as the thermoplastic resin 4 it contains, then the burst pouch 5 will peel out of the injection tube 6 after the injection molding process is completed. Furthermore, if the burst pouch 5 is made of material that is not the same as the thermoplastic resin 4 that it contains, it may have a notch, weakened spot, crimp, or incomplete perforation on the distal end approximating the nozzle opening 7 of the injection tube 6 to facilitate rupture of the molten thermoplastic resin 4 into the nozzle 7.

The thermoplastic resin 4 used in this invention may be prepackaged by a supplier into the delivery means such as a containment/delivery means 5 as pictured in FIG. 2. The thermoplastic resin 4 may also be sold to a dental laboratory in bulk. If it is supplied in bulk, dental laboratory personnel would dispense a predetermined amount of thermoplastic resin 4 into a containment/delivery means such as a foil bag or burst pouch 5, prior to an injection molding procedure.

Figure 1A:
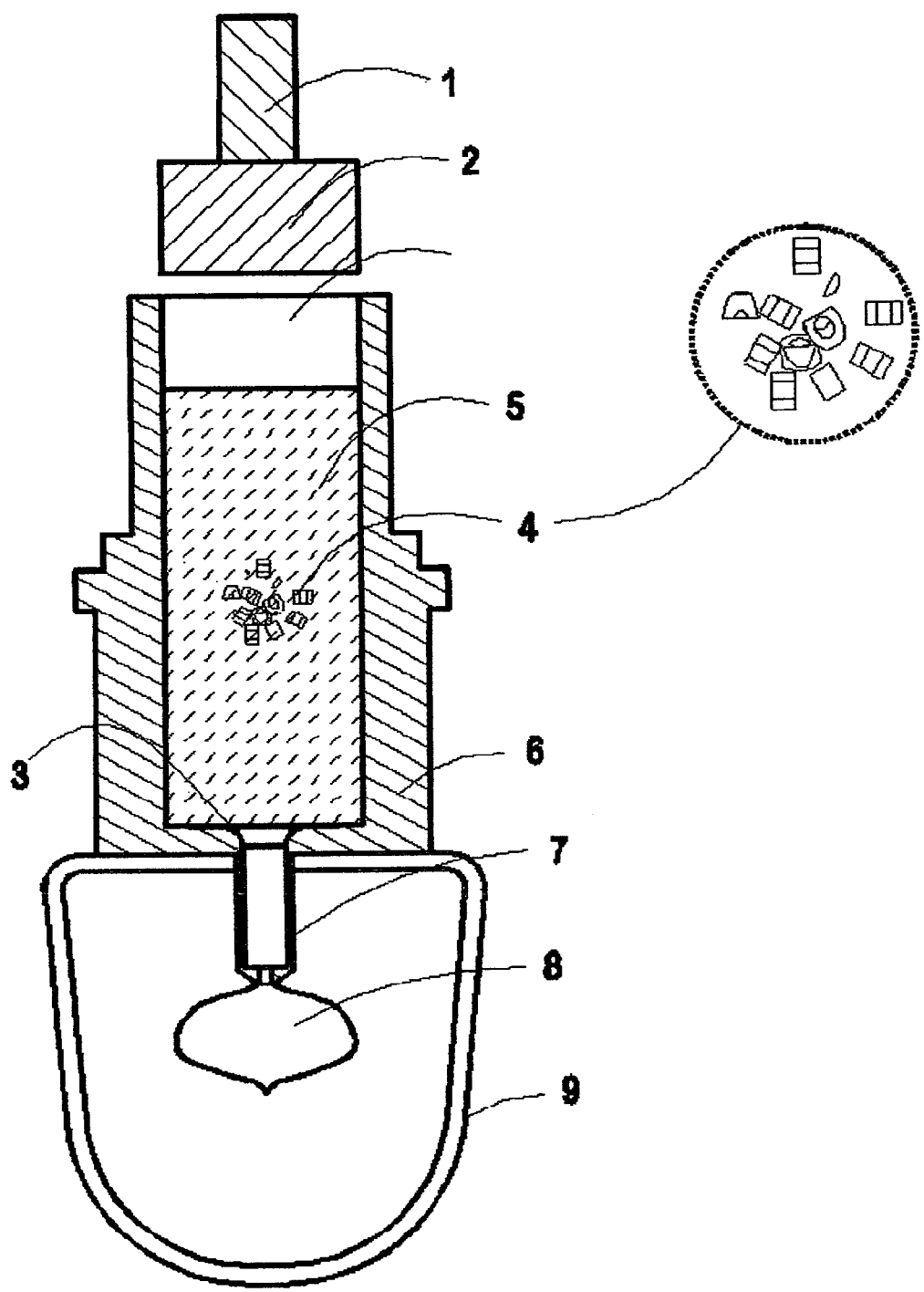
FIG. 1*a* shows the thermoplastic resin in pellet form.

Yet another containment/delivery means 5 for the bulk thermoplastic resin 4 is in solid pellet form shown in FIG. 1*a* This is embodied as a small disc shown in FIG. 5 that is placed adjacent to the nozzle opening 7 and has a weakened center that will open under pressure and allow the fluid thermoplastic resin material to pass through the nozzle 7 into the mold 8 and the flask 9 during the injection molding procedure. The disc can be made out of a higher fusion temperature resin or metal, and will have a weakened center with a stamp, incomplete perforation or crimp. The disc also may have a center area that has small laser cut into cross hatches that will facilitate its rupture. After rupture of the disc, the flow of the material will be from the injection tube 6 into the nozzle 7 and finally into the mold 8 contained in the flask 9.

In all cases, injection tube nozzle 7 is inserted, attached or threaded into the injection tube 6 and is removable therefrom. The injection tube nozzle 7 is made of material selected from the group consisting of metal, Teflon, or any resin material sufficient to withstand the fusion temperature of the molten thermoplastic resin 4.

The containment/delivery means 5 may consist of several types of metal foil, be coated with polyester film (such as Mylar), or may be heat sealable. If the containment/delivery means 5 is burst pouch, it may consist of the same type of materials and may be prepackaged or pre-dispensed and sealed by the dental laboratory prior to injection molding. The burst pouch 5 may be made from a fabric material. If the thermoplastic resin 4 is dispensed in a syringe (not shown), the syringe material must be able to withstand the fusion temperature of the thermoplastic resin 4 it contains.

In the preferred embodiment mentioned above wherein the containment/delivery means 5 and the thermoplastic resin 4 are the same material, the thermoplastic resin 4 being used for natural-looking prostheses are pre-colored in precise tooth shades, gingival shades and the like. This is done in accordance to specifications in use by the modern dental industry, such as standard or 3D Vita shades, plus extended range bleached shades to match whitened or bleached teeth. The color of the thermoplastic resin 4 would by necessity need to exactly match the color of the tooth it is replacing. Vita shades for teeth are used for making dental prostheses with various color hues. The density of the color present for each hue is classified on a numerical scale with lower numbers indicating less color density and higher numbers indicating higher color density.

The dental prostheses 8 that are made from the materials and methods of the present invention include indirect dental fillings, inlays, onlays, overlays, partial and full crowns, bridges, partial dentures, full dentures, occlusal appliances, orthodontic appliances, mouthguards, snoring and sleep apnea appliances.

The use of monochromatic thermoplastic resin 4 results in a prosthesis 8 that is monochromatic. To create a prosthesis 8 with a gradient of colors, which would be more aesthetic since natural teeth have a color gradient and are not monochromatic, the thermoplastic material 4 could be pre-packaged with a multitude of colors or shades. It could also be placed into the injection tube 6 or containment means 5 in such order as to create a color gradient within the finished prosthesis 8. Furthermore, the thermoplastic material 4 may be preformed into an ingot (not shown) that precisely fits the injection mold machine injection tube 6 and does not require any type of intermediate containment means. The ingot may also have a variety of colors to create a more natural appearing prosthesis 8.

The color gradient for the prostheses 8 made by this invention may also be accomplished by strategically placing the correct colored materials into the injection tube 6, employing a variety of containment means 5. Using a multi-colored containment disc previously mentioned, the correct color of ingots or pellets may then be placed in sequential order into the injection tube 6 to create the desired color gradient. This procedure improves natural appearance of the prosthesis 8.

In traditional cold press of dental prostheses techniques, (prior art), the materials used are monomer/polymer acrylic resins. These are often porous and may contain as much as 35% free acrylic monomer. The porosity often results in discoloration and odor absorption of the prosthesis 8 as well as bacterial and fungal growth.

It is estimated that about 12% of the population is allergic to acrylic monomer. The thermoplastic resins 4 of the instant invention are not porous and they have a minimal (about 0.12%) amount of residual free monomer. Acrylic monomers are a known toxin and irritant, and include methyl methacrylate (MMA), and polymethyl methacrylate (PMMA). The thermoplastic resins 4 of the instant invention are less toxic and are also less likely to accumulate stain and are stronger (more resistant to breaking, chipping, cracking under normal use). This results in a much better dental prosthesis 8 for the patient.

The thermoplastic resins usable in the invention are homo-polymer and co-polymer acetal, acrylic, polycarbonate, polystyrene, polyester, polyamide, polyethylene, polypropylene, polysulfone, polyphthalamide, nylon co-polymers and compatible mixtures thereof.

Furthermore the thermoplastic resins used in this invention may contain other modifiers that provide additional desired properties not previously used in the dental industry. The thermoplastic resinous materials 4 from which the dental prostheses 8 of this invention are made may be modified with materials for strength, wear resistance, ultraviolet light resistance, antistatic, or be impact modified. Additives for these and other purposes are selected from the group consisting of glass-fiber coupled, glass bead filled, and mineral coupled. The glass fiber and glass bead modifiers increase the strength and wear resistance, while the mineral coupled resins have greater impact resistance and are less conductive of electricity.

Additional additives may be added to protect the color stability and UV resistance of the prosthesis 8. For example, when acetal copolymer is employed as a thermoplastic resin 4 of this invention, a UV resistant Celcon (Hoechst-Celanese) acetal has been developed. This or other performance additives may be added to the thermoplastic resin 4 when molding.

Since prior art cold press equipment is readily available in almost all dental laboratories, this invention allows virtually all dental laboratories to fabricate prostheses 8 from thermoplastic resins 4 without the expense of acquiring special hot press injection molding machines and materials.

Figure 4:
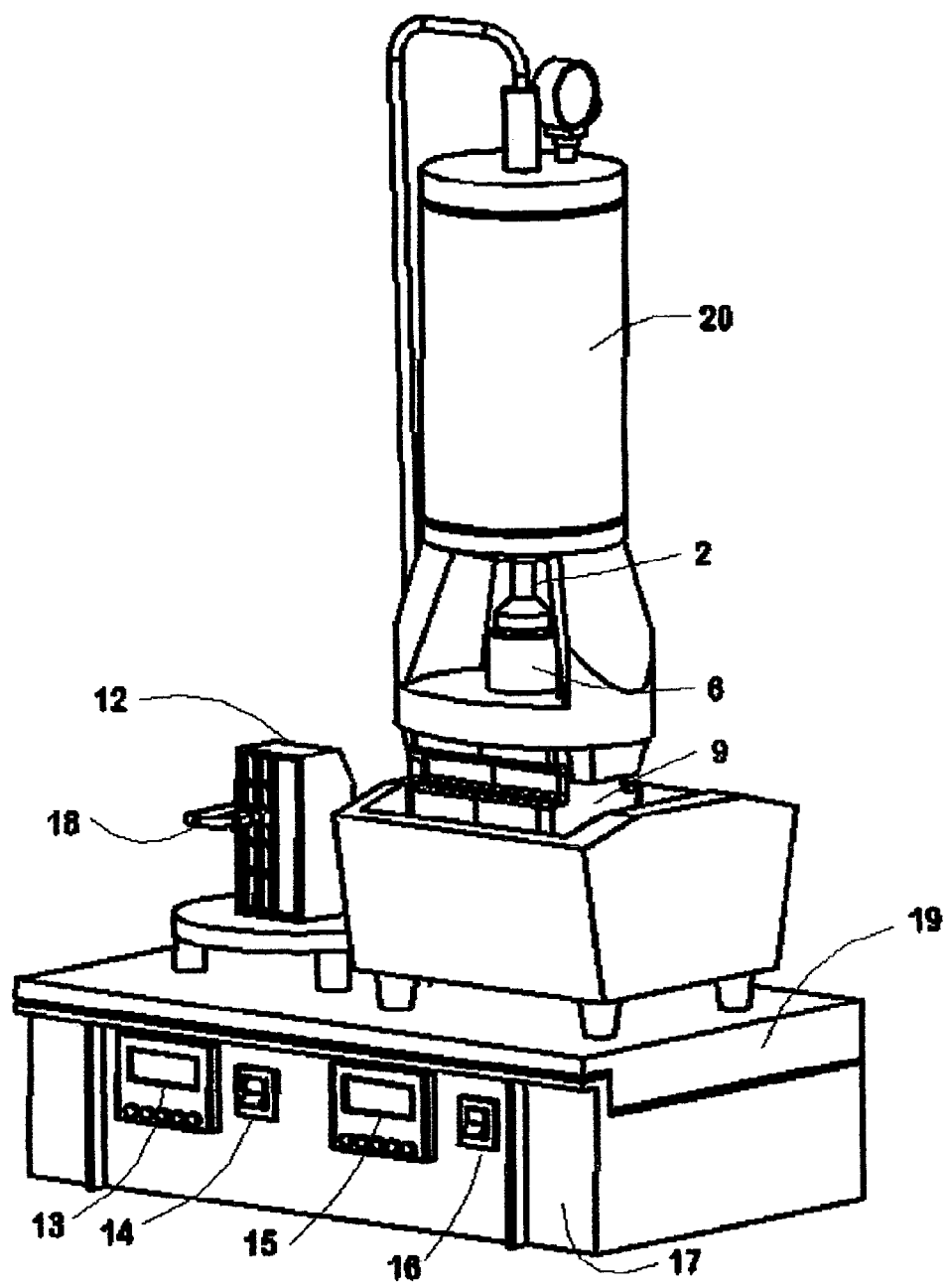
FIG. 4 is the cold press injection molding machine of the instant invention.

As seen in FIG. 4, the injection tube 6 can be heated by means of a thermal jacket 12 placed around the said tube 6. As seen in the figure, the thermal jacket 12 has a separate power supply and control mechanism 19 to control the temperature of the injection tube 6 and thermoplastic resin 4 it contains to achieve fusion of the thermoplastic resin 4. The thermal jacket 12 is connected to the power and control mechanism 19 by a wiring harness 18, and the control mechanism 19 may act as supply for multiple of thermal jackets 12, thereby increasing the effective production output of a single cold press machine 20. The thermal jacket 12 may be designed to remain on the injection tube 6 during the injection process, and may be designed to fit partially over the flask 9 to impart heat to preheat the flask 9 and mold 8 prior to and/or during the injection process.

EXAMPLE

Procedures for Using the Cold Press Machine 20 of the Instant Invention to Fabricate a Dental Prosthesis When creating a dental prosthesis for a patient, following diagnosing and treatment planning, the dentist makes the appropriate preparation of the mouth, teeth and related structures for the final prosthesis. The dentist first takes an impression employing a plastic material of the patient's mouth. The dentist will take impressions of both arches, the maxilla and mandible, and a correlation bite registration of the two jaws.

From these impressions, laboratory models are made by pouring the impressions with plaster or stone that hardens and, after hardening, is easily removed from the soft plastic impressions to faithfully replicate the patient's upper and lower jaws, including the teeth and adjacent gingival areas.

The stone or plaster models are then sent to a dental laboratory where a laboratory technician can manufacture the dental prosthesis 8. The dental laboratory technician creates a wax prosthesis, and place the prosthesis 8 in an investment stone (not shown) and sets the material into a metal dental flask 9. The technician then places the flask 9 into a burn-out oven (not shown) to heat and remove the wax, leaving a negative mold of the prosthesis 8 internally in the stone mold and flask 9. The technician then prepares a desired color or gradient of colors of thermoplastic resin 4 and places it into a containment/delivery means such as a foil bag or burst pouch 5, and places the selected thermoplastic resin 4 into the injection tube 6. The injection tube 6 is then placed into a standard dental laboratory oven (not shown), accessory oven (not shown) or thermal jacket 12 and heated to the fusion temperature of the thermoplastic resin 4 material selected. The metal flask 9 is also heated to a desired temperature, substantially lower than the fusing temperature of the thermoplastic resin 4.

When the desired temperatures are achieved, the flask 9 and injection tube 6 are placed into a cold press injection molding machine 20 of this invention and the molten thermoplastic resin 4 is injected by pressure into the flask 9 containing the mold of the prosthesis 8. The prosthesis is then created. Following a sufficient cooling period under continued pressure, the flask 9 is separated and the dental prosthesis 8 is removed from the stone cast (not shown). The prosthesis 8 is then polished and finished whereupon it is returned to the dentist's office for final adjusting and insertion into the patient's mouth.

SCOPE OF THE INVENTION

The above presents a description of the best mode contemplated of carrying out the present invention, and of the manner and process of making and using it, in such full, clear, concise, and exact terms as to enable any person skilled in the art to which it pertains to make and use this invention. This invention is, however, susceptible to modifications and alternate constructions from that discussed above which are fully equivalent. Consequently, it is not the intention to limit this invention to the particular embodiments disclosed. On the contrary, the intention is to cover all modifications and alternate constructions coming within the spirit and scope of the invention as generally expressed by the following claims, which particularly point out and distinctly claim the subject matter of the invention.

The invention claimed is:

1. A cold press injection molding apparatus for fabricating dental prostheses from thermoplastic resinous materials comprising:
   a) a piston that pushes a plunger to activate the injection molding operation;
   b) a quantity of thermoplastic resin out of which the prosthesis is made;
   c) a flexible containment and delivery means selected from the group consisting of a flexible metal foil bag, a foil burst pouch, a syringe, an ingot, a resin cylinder, fiberglass, metal, polyester film, fabric, a disc, and woven material that holds said thermoplastic resin until delivery into an injection tube which is pre-measured and independently heated in an amount appropriate to the prosthesis being fabricated;
   d) an injection tube which acts as a heat sink made from material able to withstand the fusion temperature of the thermoplastic resin;
   e) a nozzle on the end of said injection tube which delivers the fused thermoplastic resin into a dental flask, and made from a material able to withstand the fusion temperature of the thermoplastic resin;
   f) a mold in the flask from which the prosthesis is formed from fused thermoplastic resin whereby the fabricated prosthesis is identical in shape and dimensions to the mold from which it was made.

2. The apparatus of claim 1 wherein the thermoplastic resinous materials from which the dental prosthesis is made are selected from the group consisting of homo and co-polymer acetal, acrylic, polycarbonate, polystyrene, polyester, polyamide, polyethylene, polypropylene, polysulfone, polyphthalamide, and nylon co-polymers and compatible mixtures thereof.

3. The apparatus of claim 2 wherein the thermoplastic resinous materials from which the dental prosthesis is made is modified with materials for strength, wear resistance, ultraviolet light resistance, antistatic properties, and impact modification with materials selected from the group consisting of coupled glass-fiber, glass bead filled, and mineral coupled.

4. The apparatus of claim 2 wherein the thermoplastic resin is independently heated outside of the cold press injection mold in an apparatus selected from the group consisting of a standard dental laboratory oven, an accessory heating oven, and a thermocouple jacket.

5. The apparatus of claim 4 wherein the thermoplastic resin is heated in a thermocouple jacket placed around the injection tube and heated to the melting temperature of the thermoplastic resin.

6. The apparatus of claim 1 wherein the melted thermoplastic resin is removed from the independent heating means, poured into the injection tube which sends it through the nozzle where it is received by the mold to form a dental prosthesis.

7. The apparatus of claim 1 wherein the dental prostheses fabricated are made for purposes selected from the group consisting of indirect dental fillings, inlays, onlays, overlays, partial and full crowns, bridges, partial dentures, full dentures, occlusal appliances, orthodontic appliances, mouthguards, snoring appliances, and sleep apnea appliances.

8. The apparatus of claim 1 wherein the injection tube is made of metal is selected from the group consisting of aluminum, stainless steel, and brass, copper and alloys thereof.

9. The apparatus of claim 6 wherein the injection tube nozzle is removable and reattachable from the injection tube by means of insertion or threading into the injection tube.

10. The apparatus of claim 9 wherein the nozzle is made from a material that can withstand the fusion temperature of the molten thermoplastic resin it contains.

11. The apparatus of claim 1 wherein the amount of thermoplastic resinous materials from which the dental prosthesis is prepackaged by a supplier to dental labs and dental offices.

12. The apparatus of claim 1 wherein the flexible containment and delivery means is a disc.

13. The apparatus of claim 12 wherein the bulk thermoplastic resinous material is in solid pellet form and held in the apparatus by a small disc that is placed adjacent to the nozzle opening and which has a weakened center that opens under pressure and allows the thermoplastic resinous material to pass through the nozzle into the mold and the flask to fabricate the desired prosthesis.

14. The apparatus of claim 12 wherein fabrication of dental prostheses is facilitated by the rupture of the disc that firstly holds a quantity of thermoplastic resinous material and secondly releases it.

15. The apparatus of claim 14 wherein the disc contained therein is made of metal and has a center that is weakened with small laser cut into cross hatches that facilitate its rupture.

16. The apparatus of claim 14 wherein the flow of the thermoplastic resinous material starts from ruptured disc to the injection tube and then flows into the nozzle and finally flows into the mold that is contained in the flask.

17. The apparatus of claim 16 wherein the prosthesis is fabricated from thermoplastic resin to make prostheses selected from the group consisting of a temporary fixed bridge, a provisional fixed bridge, the substructure framework for a partial denture, and the baseplate of a partial denture, and the baseplate of a complete denture.

* * * * *